United States Patent [19]

Yamauchi et al.

[11] Patent Number: 4,681,978

[45] Date of Patent: Jul. 21, 1987

[54] PROCESS FOR PRODUCING 2,6-NAPHTHALENEDICARBOXYLIC ACID

[75] Inventors: Takashi Yamauchi; Shoichiro Hayashi; Atsushi Sasakawa, all of Iwaki, Japan

[73] Assignee: Kureha Kagaku Kogyo Kabushiki Kaisha, Tokyo, Japan

[21] Appl. No.: 770,249

[22] Filed: Aug. 28, 1985

[30] Foreign Application Priority Data

Sep. 10, 1984 [JP] Japan ................................ 59-189442

[51] Int. Cl.$^4$ ............................................ C07C 51/265
[52] U.S. Cl. ................................................ 562/413
[58] Field of Search ................................ 562/413, 416

[56] References Cited

FOREIGN PATENT DOCUMENTS 0666709 2/1952 United Kingdom ................ 562/413
2164337 3/1986 United Kingdom .

OTHER PUBLICATIONS

Fortuin et al., Petroleum Refiner, vol. 38, No. 6, 1959, pp. 189–193.
Chem. Abstracts, vol. 85, abstract No. 46254u, 1976 (abstract of Japan Kokai 76/6953).
Chem. Abstracts, vol. 79, abstract No. 136893g, 1973 (abstract of JP 73/27318).
Chem. Abstracts, vol. 87, abstract No. 134813x, 1977 (abstract of JP Kokai 77/17453).

Primary Examiner—James H. Reamer
Assistant Examiner—Patricia M. Scott
Attorney, Agent, or Firm—Oblon, Fisher, Spivak, McClelland & Maier

[57] ABSTRACT

Disclosed herein is a process for producing 2,6-naphthalenedicarboxylic acid, comprising (1) oxidizing 2,6-diisopropylnaphthalene in a lower fatty acid as a solvent in the presence of a catalyst comprising a water-soluble cobalt salt and/or a water-soluble manganese salt in an amount of at least 0.5 gram-atom of Co and/or Mn to 1 mol of 2,6-diisopropylnaphthalene by an oxygen-containing gas, thereby obtaining isopropylnaphthalene-monocarboxylic acid and (2) further oxidizing the thus obtained 6-isopropyl-2-naphthoic acid in the lower fatty acid in the presence of the catalyst comprising a water-soluble cobalt salt and/or a water-soluble manganese salt in an amount of from 0.0025 to 0.12 gram-atom to 1 mol of 6-isopropyl-2-naphthoic acid by the oxygen-containing gas, thereby obtaining 2,6-naphthalenedicarboxylic acid.

6 Claims, No Drawings

PROCESS FOR PRODUCING 2,6-NAPHTHALENEDICARBOXYLIC ACID

BACKGROUND OF THE INVENTION

The present invention relates to a process for producing 2,6-naphthalenedicarboxylic acid which is useful as the starting material for producing polyester resins by the oxidation of 2,6-diisopropylnaphthalene.

Hitherto, as the aromatic dicarboxylic acid used as the starting material in the production of polyester resins, terephthalic acid obtained by using p-xylene as the starting material has been used and terephthalic acid is produced industrially in a large amount.

However, in recent years, there is a number of demand for improving the quality such as the heat-resistance and mechanical properties of polyester resin, and for meeting the demand, the polyester resin obtained by using 2,6-naphthalenedicarboxylic acid as the starting material instead of terephthalic acid has attracted an attention. Accordingly, the development of an industrially profitable process for producing 2,6-naphthalenedicarboxylic acid (hereinafter referred to as 2,6-NDCA) has come to be demanded.

For finding a process for producing 2,6-NDCA, studies have been carried out hitherto in line with the production of terephthalic acid, and the oxidation of each member of 2,6-dialkylnaphthalenes, for instance, 2,6-dimethylnaphthalene, 2,6-diethylnaphthalene and the like in the presence of a known catalyst has been tried. Since 2,6-dimethylnaphthalene is easily oxidizable by a process similar to that for oxidizing p-xylene, it is convertible to 2,6-NDCA in a high yield by the oxidation process while using the known catalyst (refer to Examples 1 to 3 of Japanese Patent Publication No. 59-13495 (1984)). On the other hand, there is a practical problem that 2,6-dimethylnaphthalene itself is not easily available industrially. Namely, in the process for production of 2,6-dimethylnaphthalene comprising subjecting naphthalene to dimethylation to obtain the isomeric mixture of dimethylnaphthalenes and separating 2,6-dimethylnaphthalene from the isomeric mixture of dimethylnaphthalenes, the dimethylation is not easily effected and the separation is also difficult and accordingly, 2,6-dimethylnaphthalene cannot be said to be an industrially suitable starting material for obtaining 2,6-NDCA.

Concerning 2,6-diethylnaphthalene, the production thereof is easier than that of 2,6-dimethylnaphthalene (Japanese Patent Application Laid-Open No. 51-6953 (1976)), however, the diethylation of naphthalene and the separation of 2,6-isomer from the isomeric mixture of diethylnaphthalenes are not necessarily carried out easily in an industrial scale and accordingly, also 2,6-diethylnaphthalene cannot be said to be suitable as the starting material for 2,6-NDCA.

On the other hand, in consideration of the above-mentioned situations, 2,6-diisopropylnaphthalene which is easily separated from the isomeric mixture of diisopropylnaphthalenes easily available by the diisopropylation of naphthalene has been used as the starting material for 2,6-NDCA. However, as has been disclosed in Japanese Patent Application Laid-Open No. 51-6953, oxidation of 2,6-diisopropylnaphthalene (hereinafter referred to as 2,6-DIPN) to 2,6-NDCA has been regarded extremely difficult, and any report on the production of 2,6-NDCA from the isolated 2,6-DIPN as the starting material has not been published except for the following.

There is a disclosure concerning the oxidation of diisopropylnaphthalene slightly contained in a mixture of naphthalene, 1-isopropylnaphthalene, 2-isopropylnaphthalene diisopropylnaphthalene and other compounds, into naphthalenedicarboxylic acid (refer to Japanese Patent Publication No. 48-27318 (1973)). Although the object of the above-mentioned oxidation is to obtain naphthoic acids and/or naphthalenedicarboxylic acid, the yield of naphthalenedicarboxylic acid by the disclosure was only 2.0 parts by weight to 20 parts by weight of the mixture used as the starting material.

Concerning the oxidation of aromatic hydrocarbons substituted by two isopropyl groups, for instance, it has been reported that although the oxidation of 1,4-diisopropylbenzene to monocarboxylic acid (p-isopropylbenzoic acid) is promptly carried out, the oxidation of the thus formed monocarboxylic acid to dicarboxylic acid (terephthalic acid) is difficult (refer to J. P. Fortuin et al., Petroleum Refinery, 38(6), 189–193 (1959)).

In the case of oxidation of 2,6-DIPN, the oxidizing susceptivity of 2-isopropyl group is not the same as that of 6-isopropyl group, and the oxidation of 6-isopropyl-2-naphthoic acid (formed by oxidation of 2,6-DIPN) is accompanied by the various side reactions such as ring-opening. Accordingly, it is impossible to obtain 2,6-NDCA in a high yield from 2,6-DIPN by the oxidation under one reaction condition.

Namely, the object of the present invention is to provide a process for favorably producing 2,6-NDCA which is useful as the starting material for producing polyester resin, by using as the starting material 2,6-DIPN which is easily available in an industrial scale and specifying the reaction conditions in the oxidation of 2,6-DIPN.

As a result of the present inventors' studies concerning the reaction conditions of the oxidation of 2,6-DIPN to 2,6-NDCA, it has been found that (1) the optimum reaction conditions in the reaction for oxidizing 2,6-DIPN to 6-isopropyl-2naphthoic acid (2-isopropyl-naphthoic acid) are quite different from the optimum reaction conditions in the reaction for oxidizing 6-isopropyl-2-naphthoic acid to 2,6-NDCA, and (2) the above-mentioned two reactions are carried out separately in the two steps while using the same catalyst under the same reaction conditions except for the amount of the catalyst, whereby 2,6-NDCA can be obtained from 2,6-DIPN in a high yield, in other words, in a high selectivity.

The present invention has been attained on the basis of the findings.

DETAILED EXPLANATION OF THE INVENTION

The characteristic feature of the present invention is in that a process for producing 2,6-NDCA while using 2,6-DIPN as the starting material, comprises (1) oxidizing 2,6-DIPN by a molecular oxygen-containing gas in a lower fatty acid as a solvent in the presence of a catalyst of a water-soluble salts of cobalt, a water-soluble salts of manganese or a mixture thereof in an amount of at least 0.5 gram-atom of the metal (Co and/or Mn) to 1 mol of 2,6-DIPN, preferably 0.8 to 5.0 gram-atom of the metal, under a pressure, for instance, from 3 to 50 kg/cm2 G and at a temperature of 120° to 250° C., preferably 130 to 210° C, thereby converting 2,6-DIPN into 6-isopropyl-2-naphthoic acid and then, (2) further oxidizing the thus obtained 6-isopropyl-2-naphthoic acid in the lower fatty acid as a solvent in the presence of the catalyst in an amount of from 0.0025 to 0.12 gram-atom of the metal (Co and/or Mn), preferably 0.003 to 0.06 gram-atom of the metal under a pressure, for example, from 3 to 50 kg/cm$^2$ G and at a temperature of 120 to 250° C., preferably 130° to 210° C. to obtain the object compound, 2,6-NDCA.

As the lower fatty acid used as a solvent according to the present invention, acetic acid, propionic acid, butyric acid and isobutyric acid may be mentioned, and, the amount of said lower fatty acid employed ranges from 1 to 100 parts by weight to 1 part by weight of 2,6-DIPN. Acetic acid is the preferred lower fatty acid.

The acid for forming the water-soluble salts of cobalt and the water-soluble salts of manganese is preferably an aliphatic carboxylic acid or an aromatic carboxylic acid, and for instance, acetic acid, propionic acid, butyric acid, benzoic acid, cumic acid, phthalic acid and naphthalenemonocarboxylic acid may be exemplified.

As the molecular oxygen-containing gas for use in the oxidation, air, oxygen itself or a gas prepared by diluting air or oxygen with an insert gas such as nitrogen may be mentioned.

The reaction time in the step (1) for oxidizing 2,6-DIPN into 6-isopropyl-2-naphthoic acid depends on the amount of the lower fatty acid, for instance, acetic acid, used as a solvent, the amount of the catalyst used in the reaction, the reaction temperature and the reaction pressure, However, in general, it is in a range of 0.5 to 10 hours.

Since 6-isopropyl-2-naphthoic acid is advantageously formed by oxidizing 2,6-DIPN under the abovementioned reaction conditions, the thus formed reaction mixture is subjected to treatments for isolating 6-isopropyl-2-naphthoic acid therefrom, for instance, after condensing the reaction mixture, it is extracted with a water and chloroform system, the chloroform layer is subjected to distillation to remove chloroform, and 6-isopropyl-2-naphthoic acid which may be recrystallized from a solvent such as chloroform and benzene is collected. The thus purified 6-isopropyl-2-naphthoic acid is usable as the starting material for 6-hydroxy-2-naphthoic acid in addition to the starting material for 2,6-NDCA.

The reaction time in the step (2) for oxidizing 6-isopropyl-2-naphthoic acid into 2,6-NDCA is also in the range of 0.5 to 10 hours.

Since thus formed 2,6-NDCA in the step (2) precipitates from the reaction mixture, it is collected by filtration, washed with acetic acid and then with water, and dried to be the product (2,6-NDCA) according to the present invention.

As has been explained, by carrying out the oxidation of 2,6-DIPN in the two steps respectively using the catalyst mutually different in the amount thereof, the oxidation of 2,6-DIPN into 2,6-NDCA which has hitherto been regarded as difficult is advantageously effected and accordingly it is possible to produce 2,6-NDCA which is useful as the starting material for polyester resins, in a high yield from 2,6-DIPN which is easily available industrially.

The present invention will be explained more in detail while referring to Examples as follows.

EXAMPLE 1

(1-1) Production of 6-isopropyl-2-naphthoic acid

Into a stainless-steel (SUS-316) autoclave of 20 liters in capacity, 200 g of 2,6-DIPN were introduced as the starting material together with 5 kg of acetic acid, 100 g of cobalt acetate tetrahydrate, and 200 g of manganese acetate tetrahydrate, and the inner pressure of the autoclave was raised to 30 kg/cm$^2$ G while introducing thereon gaseous nitrogen and heating the autoclave. At the time when the inner temperature of the autoclave raised to 150° C., the gaseous nitrogen was changed to a gaseous mixture of nitrogen and oxygen (90 : 10 by volume) and the reaction was carried out for 6 hours while maintaining the inner pressure of the autoclave at 30 kg/cm$^2$ G and adjusting the flow rate of the waste gas from the outlet to 200 N liters/hour.

After finishing the reaction, the introduction of the gaseous mixture was stopped, and after cooling the autoclave and purging the residual gas in the autoclave, the reaction product was taken out. By collecting a part of the reaction product, and subjecting the reaction product to analysis, it was found that the composition of the reaction product is 70.1 mol % of 6-isopropyl-2-naphthoic acid, 2.2 mol % of 2,6-naphthalenedicarboxylic acid and 7.2 mol % of the unreacted 2,6-DIPN. Namely, the selectivity of the reaction to 6-isopropyl-2-naphthoic acid was 75.5%.

After distilling the low-boiling substances such as acetic acid and water therefrom, 2.3 liters of chloroform and 1.3 liters of water were added to the reaction product to subject to extraction, and after washing the thus obtained chloroform layer with water, chloroform was distilled off to obtain the crude 6-isopropyl-2-naphthoic acid in an amount of 190 g.

By recrystallizing the thus obtained crude acid from 670 ml of benzene, 122 g of purified 6-isopropyl-2-naphthoic acid of a purity of 99.5% were obtained, and by treating the filtrate of the recrystallization thereof in a similar manner, 16 g of purified 6-isopropyl-2-naphthoic acid of a purity of 99.3% were obtained. Accordingly, the total yield of isolation of 6-isopropyl-2-naphthoic acid was 68.0%.

(1-2) Production of 2,6-NDCA

Into a stainless-steel (SUS 316) autoclave of a capacity of 200 ml, 10 g of the thus obtained 6-isopropyl-2-naphthoic acid were introduced together with 100 g of acetic acid, 0.1 g of cobalt acetate tetrahydrate and 0.2 g of manganese acetate tetrahydrate, the inner pressure of the autoclave was raised to 30 kg/cm$^2$ G while introducing gaseous nitrogen and heating the autoclave. At the time when the inner temperature of the autoclave was raised to 150° C., the gaseous nitrogen was changed to a gaseous mixture of nitrogen and oxygen (90:10 by volume), and the reaction was carried for 4 hours while maintaining the inner pressure of the autoclave at 30 kg/cm$^2$ G and adjusting the flow rate of the waste gas from the outlet to 50 N liter/hour.

After finishing the reaction, the introduction of the gaseous mixture was stopped and the autoclave was cooled, and after purging the residual gas in the autoclave, the reaction mixture therein was taken out. After collecting the precipitated 2,6-NDCA, washing the precipitate with acetic acid and water, the precipitate was dried to obtain 3.85 g of 2,6-NDCA. On the other hand, the unreacted 6-isopropyl-2-naphthoic acid remaining in the filtrate was analyzed to be 4.27 g.

Accordingly, the yield of 2,6-NDCA in the reaction was 38.1% and the selectivity was 66.5%.

EXAMPLES 2 to 5 and COMPARATIVE EXAMPLES 1 to 3

In the similar manner to the first step (1-1) of Example 1 except for the amount of introduction of the starting material and the catalyst as shown in Table 1, 6-isopropyl-2-naphthoic acid was produced. In Comparative Examples 1 to 3, the amount of the catalyst used was smaller than that used in Examples 1 to 6. The amount of introduction of the starting material, the catalyst, the reaction conditions and the yields of the objective product, by product and unreacted starting material are shown in Table 1. The thus obtained 6-isopropyl-2-naphthoic acid was further oxidized under the same conditions as in the second step (1-2) of Example 1 to 2,6-NDCA.

TABLE 1

|  | Example | | | | Comparative Example | | |
| --- | --- | --- | --- | --- | --- | --- | --- |
|  | 2 | 3 | 4 | 5 | 1 | 2 | 3 |
| Introduced amount of |
| 2,6-DIPN (part by wt.) | 10 | 10 | 30 | 10 | 10 | 10 | 10 |
| acetic acid (the same) | 100 | 100 | 100 | 100 | 100 | 100 | 100 |
| Co acetate[1] (the same) | 5 | 10 | 5 | — | 0.5 | 0.5 | 0.5 |
| Mn acetate[2] (the same) | 10 | 20 | 10 | 15 | 1 | 1 | 1 |
| Reaction conditions |
| Pressure (kg/cm$^2$ G) | 30 | 30 | 30 | 30 | 30 | 30 | 30 |
| Temperature (°C.) | 150 | 150 | 150 | 150 | 150 | 150 | 180 |
| Time (hour) | 1 | 4 | 6 | 4 | 4 | 8 | 4 |
| Flow rate of the gas (N liters/hour) | 50 | 50 | 50 | 50 | 50 | 50 | 50 |
| Yield (mol %) |
| NMCA[3] | 56.7 | 62.3 | 56.6 | 60.6 | 30.8 | 28.9 | 10.7 |
| NDCA[4] | 1.2 | 2.4 | 5.2 | 3.4 | 1.5 | 24.7 | 20.4 |
| unreacted 2,6-DIPN | 24.2 | 3.8 | 3.6 | 14.6 | 38.0 | 0 | 0 |

Notes:
[1]cobalt acetate tetrahydrate,
[2]manganese acetate tetrahydrate
[3]6-isopropyl-2-naphthoic acid
[4]2,6-naphthalenedicarboxylic acid

EXAMPLE 6

In the same procedures as in the first step (1-1) of Example 1 except for the amount of introduction of the starting material, the solvent and the catalyst and the reaction conditions as shown below, 6-isopropyl-2-naphthoic acid was produced.

Amount of introduction of
2,6-DIPN: 10 parts by weight,
acetic acid: 100 parts by weight and
Mn(OCOCH$_3$)$_2$.4H$_2$O: 15 parts by weight
Reaction conditions of
Pressure: 10 kg/cm$^2$ G
Temperature: 200° C.
Time period: 2 hours and
Flow rate of the gaseous mixture: 50 N liters/hour The yields of the compounds in the reaction mixture of the above-mentioned reaction were as follows.
6-isopropyl-2-naphthoic acid: 58.7%
2,6-naphthalenedicarboxylic acid: 3.6% and
2,6-diisopropylnaphthalene (unreacted): 12.7%

The thus obtained 6-isopropyl-2-naphthoic acid was further oxidized as in the second step (1-2) of Example 1 to obtain 2,6-NDCA.

EXAMPLE 7 and COMPARATIVE EXAMPLE 4

Ten grams of 6-isopropyl-2-naphthoic acid obtained in the first step (1-1) of Example 1 were further oxidized under the reaction conditions shown in Table 2, the results of the reaction being also shown in Table 2 which shows also the results of Comparative Example 4 wherein the amount of the catalyst was over the range of the present invention.

TABLE 2

|  | Example 7 | Comparative Example 4 |
| --- | --- | --- |
| Introduced amount of |
| NMCA[1] (part by wt.) | 10 | 10 |
| CH$_3$COOH (the same) | 100 | 100 |
| Co acetate[2] (the same) | 0.05 | 5 |
| Mn acetate[3] (the same) | 0.1 | 10 |
| Reaction conditions |
| Pressure (kg/cm$^2$ G) | 30 | 30 |
| Temperature (°C.) | 150 | 150 |
| Time (hour) | 4 | 4 |
| Flow rate of the gas (N liters/hour) | 50 | 50 |
| Yield (mol %) |
| 2,6-NDCA | 24.1 | 3.6 |
| NMCA (unreacted) | 62.0 | 76.7 |
| Selectivity to 2,6-NDCA | 63.4 | 15.5 |

Notes:
[1]6-isopropyl-2-naphthoic acid
[2]Cobalt acetate tetrahydrate
[3]Manganese acetate tetrahydrate

What is claimed is:

1. A process for producing 2,6-naphthalenedicarboxylic acid, comprising (1) oxidizing 2,6-diisopropylnaphthalene in a lower fatty acid as a solvent in the presence of a catalyst comprising a water-soluble cobalt salt, a water-soluble manganese salt, or mixture thereof in an amount of at least 0.5 gram-atom of Co, Mn or mixture thereof to 1 mol of 2,6-diisopropylnaphthalene by a molecular oxygen-containing gas, thereby obtaining 6-isopropyl-2-naphthoic acid and (2) further oxidizing the thus obtained 6-isopropyl-2-naphthoic acid in the lower fatty acid in the presence of the catalyst comprising a water-soluble cobalt salt, a water-soluble manganese salt or mixture thereof in an amount of from 0.0025 to 0.12 gram-atom to 1 mol of 6-isopropyl-2-naphthoic acid by the molecular oxygen-containing gas.

2. A process according to claim 1, wherein the oxidization in both steps is carried out as a temperature of 120° C. to 250° C. under a pressure of 3 to 50 kg/cm$^2$ G.

3. A process according to claim 1, wherein said lower fatty acid is used in an amount of 1 to 100 parts by weight to 1 part by weight of 2,6-diisopropylnaphthalene.

4. A process according to claim 1, wherein said lower fatty acid is acetic acid, propionic acid, butyric acid or isobutyric acid.

5. A process according to claim 1, wherein an acid for forming said water-soluble salts of cobalt and said water-soluble salts of manganese is an aliphatic carboxylic acid or an aromatic carboxylic acid.

6. A process according to claim 5, wherein said aliphatic carboxylic acid is acetic acid, propionic acid or butyric acid, and said aromatic carboxylic acid is benzoic acid, cumic acid, phthalic acid or naphthalenemonocarboxylic acid.

* * * * *